United States Patent [19]

Zelinka

[11] Patent Number: 5,531,960
[45] Date of Patent: Jul. 2, 1996

[54] AUTOMATED DISSOLVED OXYGEN AND BIOCHEMICAL OXYGEN DEMAND ANALYZER

[75] Inventor: Gregory A. Zelinka, Waunakee, Wis.

[73] Assignee: Madison Metropolitan Sewerage District, Madison, Wis.

[21] Appl. No.: 346,380

[22] Filed: Nov. 28, 1994

[51] Int. Cl.⁶ .................................................. G01N 31/00
[52] U.S. Cl. ...................... 422/79; 422/67; 422/68.1; 422/82.04; 435/34; 435/39; 436/50; 73/864.24; 210/96.1
[58] Field of Search .................... 422/67, 68.1, 79, 422/82.04; 73/19.1, 864.22, 864.24, 864.25; 436/50; 210/96.1, 96.2; 435/34, 39

[56] References Cited

U.S. PATENT DOCUMENTS

| | | | |
|---|---|---|---|
| 3,042,495 | 7/1962 | Wilson et al. | 422/79 X |
| 3,374,065 | 3/1968 | Suzuki | 422/79 |
| 3,510,407 | 5/1970 | Stack | 205/777.5 |
| 3,635,564 | 1/1972 | Zuckerman et al. | 356/128 |
| 3,684,702 | 8/1972 | Hartmann | 422/79 X |
| 3,731,522 | 5/1973 | Mikesell | 73/19 |
| 4,244,695 | 1/1981 | Melzer et al. | 422/79 X |
| 4,272,482 | 6/1981 | Jessop et al. | 422/65 |
| 4,318,885 | 3/1982 | Suzuki et al. | 422/68 |
| 4,363,245 | 12/1982 | Schmid | 73/864.22 |
| 4,554,839 | 11/1985 | Hewett et al. | 73/864.16 |
| 4,555,957 | 12/1985 | Frankel et al. | 73/864.14 |
| 4,680,267 | 7/1987 | Eppstein et al. | 435/289 |
| 4,751,052 | 6/1988 | Schwartz et al. | 422/100 |
| 4,948,563 | 8/1990 | Kanewske | 422/99 |
| 5,017,496 | 5/1991 | Klapwijk et al. | 436/62 |
| 5,025,927 | 6/1991 | Garg | 206/527 |
| 5,132,094 | 7/1992 | Godec et al. | 422/68.1 |
| 5,260,872 | 11/1993 | Copeland et al. | 364/413.07 |
| 5,309,959 | 5/1994 | Shaw et al. | 141/130 |
| 5,324,480 | 6/1994 | Shumate et al. | 422/63 |

OTHER PUBLICATIONS

Skalar SP100 Robotic Analyser and its applications, Nov. 1993, Netherlans.
Hurst Motors and Stepping Motor Controls, Catalog 5000, 35th Ed. Hurst Manufacturing Division, Emerson Electric Company, Princeton, IN.
Standard Methods for the Examination of Water and Wastewater, 18th ed. 1992, edited by Arnold E. Greenberg et al.

Primary Examiner—Robert J. Warden
Assistant Examiner—Harold Y. Pyon
Attorney, Agent, or Firm—DeWitt Ross & Stevens

[57] ABSTRACT

An automated method and apparatus for determining the dissolved oxygen (DO) content and the biochemical oxygen demand (BOD) of multiple test samples includes a sample set containing several test sample containers, a robotic arm capable of motion toward the sample set, DO probes releasibly attached to the robotic arm, and a programmable computer interfaced with the robotic arm and controlling the robotic arm. To measure the DO of test samples within the test sample containers, DO probes (which are connected to respective DO meters) are positioned adjacent a set of test sample containers and inserted within, the DO meters determine the DO within the test sample containers, the DO values are recorded by use of a programmable computer, and the DO probes are then removed from the set of test sample containers. The BOD may then be calculated by sealing the set of test sample containers, incubating the set of test sample containers for a predetermined time period, removing the seals on the set of test sample containers, and repeating the DO measurement to obtain a final DO. The BOD values of the test samples may then be calculated using the initial and final DO values.

22 Claims, 4 Drawing Sheets

AUTOMATED DISSOLVED OXYGEN AND BIOCHEMICAL OXYGEN DEMAND ANALYZER

FIELD OF THE INVENTION

The present invention relates generally to an apparatus and method for measuring dissolved oxygen (DO) and biochemical oxygen demand (BOD) in liquid samples. More particularly, the present invention relates to a computer controlled robotic instrument and software system designed to automate the reading of DO test values and the calculation of BOD values for various liquid samples.

BACKGROUND OF THE INVENTION

The Biochemical Oxygen Demand (BOD) test is a commonly used test in the waste water management field for determining the amount of oxygen depletion that a sample will exert over a given period of time. Thus, the BOD of a waste sample is a measure of its strength and can be used to assess the impact of the waste on a receiving body of water. A standard BOD test involves measuring the initial dissolved oxygen (DO) concentration of a sample with specified volume, and then measuring it again at a later time, generally 5 days later. This information is then used to calculate the amount of oxygen depletion that occurred relative to the sample.

Several prior art references exist which disclose apparatuses and methods for determining oxygen rate consumption or biochemical oxygen demand in continuous flow systems or currents. For example, U.S. Pat. No. 3,374,065, issued to Suzuki, discloses an apparatus for continuously detecting and estimating BOD values in an existing source such as a drainage or river. The apparatus comprises a tube container for testing, means for injecting the sample material into the container, means for injecting a non-organic acid into the container to form a mixture, means for mixing and heating the mixture, means for detecting a low pH which causes the non-organic acid injecting means to close, means for injecting an alkaline and showing the increase in pH, and measuring means to determine the BOD.

U.S. Pat. No. 3,731,522, issued to Mikesell, describes a method and apparatus for determining oxygen rate consumption in sewage. The apparatus comprises an airtight container having an inlet and outlet, pump means for circulating sewage through the container at a constant flow rate, and sensing means for measuring the amount of dissolved oxygen in the sewage at both the inlet and outlet.

Another apparatus and method for determining oxygen rate consumption in a continuous current is described in U.S. Pat. No. 5,017,496 issued to Klapwijk et al. The Klapwijk et al. patent discloses a method comprising the steps of 1) measuring the oxygen content of a sample by passing it in a first direction past a predetermined measurement location and taking a first measurement before the continuous flow enters a given chamber and 2) reversing the continuous flow past the predetermined measurement location in a second direction and taking a second measurement after the continuous process flow has resided in the chamber.

U.S. Pat. No. 5,025,927, issued to Garg, discloses a respirometer apparatus for determining the BOD of less dilute wastewater samples than those used in standard BOD test procedures. The preferred embodiment includes a chamber having walls formed from an oxygen permeable membrane and a frame structure. Two sheets of the membrane are heat-sealed to the frame structure leaving a collapsible opening to communicate with the chamber's interior. The frame structure comprises a base plate and cover plate which are held apart from one another by supports. Inlet and outlet holes are provided in the cover and base plates to accommodate the BOD measurements of continuous flow systems.

Other prior art references disclose systems for measuring the DO and BOD of non-continuous flow liquid samples. For example, U.S. Pat. No. 3,635,564, issued to Zuckerman et al., discloses a system for measuring the organic content of water using a refractometer. Also, U.S. Pat. No. 4,244,695, issued to Melzer et al., discloses a method for quantitatively determining the total oxygen demand of water containing oxidizable matter by continuous evaporation of the water in the presence of oxygen at a temperature of about 900° C.

All of the previously described references fail to disclose an automated system for testing the DO and BOD values of multiple samples. However, several automated test systems are known in various fields of art. For example, U.S. Pat. No. 5,260,872, issued to Copeland et al., describes an automated testing system which includes a robotic arm as well as a programmable computer for functions such as controlling, dispensing, mixing, moving operations, and recording. This reference is directed to an automated system for quality testing samples for a blood-clot dissolving product. Computer software is programmed to provide all of the machine control functions including robotic arm functions, pipetting functions, and the collection and filing of resulting data.

Finally, Applicant is aware of one automated BOD analyzer produced by Skalar, Inc., located in the Netherlands. Skalar's robotic analyzer includes a computer-controlled robotic manipulator system. Samples are loaded on a transport rack which is moved via a rail system to manipulators which then perform a series of tasks on the samples. A series of measuring instruments interface with the robotic manipulator system to measure various parameters. The computer then calculates and displays results.

Although Skalar's automated instrument does perform DO/BOD determinations, Skalar's system does not possess the ability to utilize multiple vendors' DO probes and meters. In addition, Skalar's automated instrument does not possess the ability to utilize multiple probes or rinse the probes between rows of samples without using a dedicated wash area.

Accordingly, there is a need for an automated DO and BOD analyzer which increases the analytical speed for determining DO and BOD values while making use of the analyst's existing equipment, e.g., DO meters and BOD bottles already in inventory.

SUMMARY OF THE INVENTION

It is a principal object of the present invention to provide an automated method and apparatus for analyzing the DO and BOD values of various test samples.

It is a further object of the present invention to provide an automated method and apparatus for analyzing the DO and BOD values of test samples which is capable of utilizing DO probes made by different vendors.

It is a still further object of the present invention to provide an automated method and apparatus for analyzing the DO and BOD values of test samples which utilizes multiple probes at the same time, thereby increasing the analytical speed of the apparatus.

It is yet a further object of the present invention to provide an automated method and apparatus for analyzing the DO and BOD values of test samples which is capable of utilizing different types of test sample containers, DO meters/probes, and other such equipment from various vendors rather than a single one.

It is still a further object of the present invention to provide an automated method and apparatus for analyzing the DO and BOD values of test samples which includes a quick and easy means for rinsing the DO probes between sample sets.

It is still a further object of the present invention to provide an automated method and apparatus for analyzing the DO and BOD values of test samples which includes computer software capable of allowing extensive interfacing by the analyst.

It is still a further object of the present invention to provide an efficient and low cost method and apparatus which automatically analyzes the DO and BOD values of multiple test samples.

The automated testing apparatus for determining the DO and BOD values of test samples generally comprises a frame structure, a sample set which contains several test sample containers and which rests adjacent to the frame structure, and a moveable robotic arm which is supported by the frame structure and which is adapted to move towards and away from the sample set. The robotic arm also includes attachment means for releasibly attaching a DO probe to the robotic arm in such a position that the DO probe, once releasibly attached, may communicate with a test sample container within the sample set when the robotic arm moves towards the sample set, and control means for controlling the robotic arm.

The automated testing apparatus for determining the DO and BOD values of test samples may also comprise a tray adapted to contain rows of multiple test sample containers, wherein the rows are oriented in a parallel array along a linear path, and also a movable robotic arm located above the tray which may translate downward towards the tray and upward away from the tray and also in a dimension generally parallel to the linear path. The robotic arm also includes attachment means for releasibly attaching DO probes onto the robotic arm, and rinsing means for rinsing DO probes which are releasibly attached to the robotic arm.

The automated method for analyzing the DO values of a set of test samples, each of which is contained within a test sample container, generally comprises the steps of simultaneously positioning several DO probes, each of which is interfaced to one of several DO meters, each in communication with one of the test samples by use of a moveable robotic arm; determining DO values of the test samples by use of the DO meters; receiving, recording, and calculating data received from the DO meters by use of data means; and removing the DO probes from the test samples by transporting the robotic arm away from the test samples.

Further, a method for determining BOD values of the set of test samples comprises performing the steps of the aforementioned method of analyzing DO values to obtain an initial DO value, followed by the steps of placing seals on the test sample containers; incubating the test samples for a period of time; removing the seals on the test sample containers; repeating the steps of the aforementioned method of analyzing DO values to obtain a final DO value; and calculating BOD values of the test samples using the initial and final DO values.

The objects and advantages of the invention will appear more fully from the following detailed description of the preferred embodiment of the invention made in conjunction with the accompanying drawings.

DETAILED DESCRIPTION OF THE INVENTION

The Automated DO/BOD Analyzer Apparatus

With reference to the drawings, wherein reference numbers identify similar features throughout the Figures, an automated DO/BOD analyzer is shown at 10. The automated DO/BOD analyzer 10 is modular in design, and its three main components are a measurement, analysis, control, and storage (MACS) system 11, a robotic sampling system 12, and a rinse reservoir 13.

The MACS system 11 includes a personal computer (PC) 14, which is known to the art. The PC 14 may include a PC monitor 15, a printer (not shown), and one or more PC disk drives 16. The PC 14 is also equipped with a data acquisition board (not shown), which enables it to perform digital/analog conversion procedures in conjunction with a signal termination box 17. The PC 14 is thus able to communicate with either digital or analog inputs, allowing a variety of devices to interface with the PC 14.

The robotic sampling system 12 includes DO probes 20 known to the art, which will be discussed below. The MACS system 11 may include two types of data means for receiving and processing data from the probes 20 and inputting the data to the PC 14. In the preferred embodiment, DO meters 18, which are known to the art, observe dissolved oxygen (DO) measurement readings sensed by probes 20. These DO readings are input to the PC 14 when the DO meters 18 are connected thereto by DO meter cables 19. The DO meters 18 may also have the ability to supply output in digital or analog form, which facilitates their communication with the PC 14. Such is the case with the DO meters 18 of the preferred embodiment, which are YSI Model 64 and 65 ARC dissolved oxygen meters. Alternatively, the DO meters 18 may be eliminated and the probes 20 may be powered and supply analog input directly to the PC 14 and signal termination box 17. The signal termination box 17 may then convert the probe 20 signals to digital form so the PC 14 may observe them and convert them to DO measurements by use of a suitable algorithm. The DO readings received by the PC 14 may later be used to calculate BOD, a step which will be detailed later in this discussion.

The robotic sampling system 12 is supported by a frame 22, which provides structural support for the system. The frame 22 surrounds a robotic arm 21, which in turn supports the probes 20 and transports them to different locations where DO readings may be taken. The probes 20 are typically rod-like wands with 6–8 inch length and a diameter of 2 inches or less, having probe tips 51 with a tapered sensor apparatus (and sometimes a stirring mechanism) designed to fit within a standard test sample container. The robotic arm 21 is positioned by the robotic sampling system 12 so that the probe tips 51 of the probes 20 may contact the test samples and send raw signals to the DO meters 18 or signal termination box 17 and PC 14 for conversion to a DO measurement.

The robotic arm 21 includes attachment means for attaching the probes 20 to the robotic sampling system 12. In the preferred embodiment of the automated DO/BOD analyzer 10, this is done by the means of mounting plates 60, which support the probes 20 as they rest within the probe apertures 61 illustrated in FIG. 4. The probe apertures 61 can accommodate several differently-sized and shaped probes 20 supplied by different manufacturers. The probes 20 of the preferred embodiment are YSI Model 5730 self-stirring DO probes. Other attachment means such as spring-loaded clips, clamps, adhesives, and fasteners may also be used within the automated DO/BOD analyzer 10.

The robotic sampling system 12 also includes a robotic drive system 23, which translates the robotic arm 21, and the probes 20 within, towards the front of the frame 24 or the rear of the frame 25. The robotic drive system 23 may also elevate the robotic arm 21 towards the top of the frame 26 or lower it towards the bottom of the frame 27. The entirety of the robotic sampling system 12 is supplied with electricity by the power supply 28, which is mounted to the frame 22 at the rear of the frame 25. The robotic drive system 23 is operated by control means in the form of the PC 14 and software running thereon.

Translational movement of the robotic arm 21 within the robotic drive system 23 is accomplished by the action of a horizontal drive motor 29 on a horizontal drive track In the preferred embodiment, the horizontal drive motor 29 is an SL4013-001 AC synchronous linear actuator manufactured by Hurst. The horizontal drive track 23 is an Acme screw which supports the travel of a threaded rotor that is incorporated into the horizontal drive motor 29. When the horizontal drive motor 29 is actuated, the motor and the entire robotic drive system 23, with the robotic arm 21 attached, travel along the horizontal drive track 30. The robotic drive system 23 is equipped with translation wheels 31, which roll within a wheel track 32, in order to assist the smooth motion of the robotic drive system 23 towards the front of the frame 24 or the rear of the frame 25. The PC 14 is equipped to sense when the robotic drive system 23, and thus the robotic arm 21, has reached the front of the frame 24. This is indicated when the PC 14 receives a signal from a frontward stop switch 33, which is triggered by the adjustable stop collar 34. It may also detect when the robotic drive system 23 has reached the rear of the frame 25 when the rearward stop switch 35 contacts the adjustable start collar 36. The adjustable start collar 36 and adjustable stop collar 34 may be positioned at different points on the horizontal drive track 30 to alter the distance the robotic arm 21 may translate in the horizontal direction.

In similar fashion, a vertical drive motor 37 drives the robotic arm 21 upwards or downwards within the robotic drive system 23 by use of the actuator arm 38. As it does so, vertical slides 59 guide the motion of the robotic arm 21. In the preferred embodiment, the vertical drive motor 37 is also a Hurst SL4013-001 AC synchronous linear actuators with the actuator arm 38 comprising a rotor incorporating an Acme nut that travels the vertical drive screw. The PC 14 may detect when the robotic arm 21 is in the upper position when an adjustable vertical motion stop collar 39 contacts an upper stop switch 40. Likewise, the lower position of the robotic arm 21 may be sensed when the vertical motion stop collar 39 triggers a lower stop switch 41.

While the horizontal drive motor 29 and horizontal drive track 23, and the vertical drive motor 37 and actuator arm 38, position the robotic arm 21 by means of screw actuated motion, other types of actuation may function equally well and are considered to be within the scope of this invention. For example, the horizontal drive motor 29 and horizontal drive track 23, and/or the vertical drive motor 37 and actuator arm 38, may be replaced by slides/actuators driven by pneumatic, hydraulic, or electromagnetic means.

Figure 1:
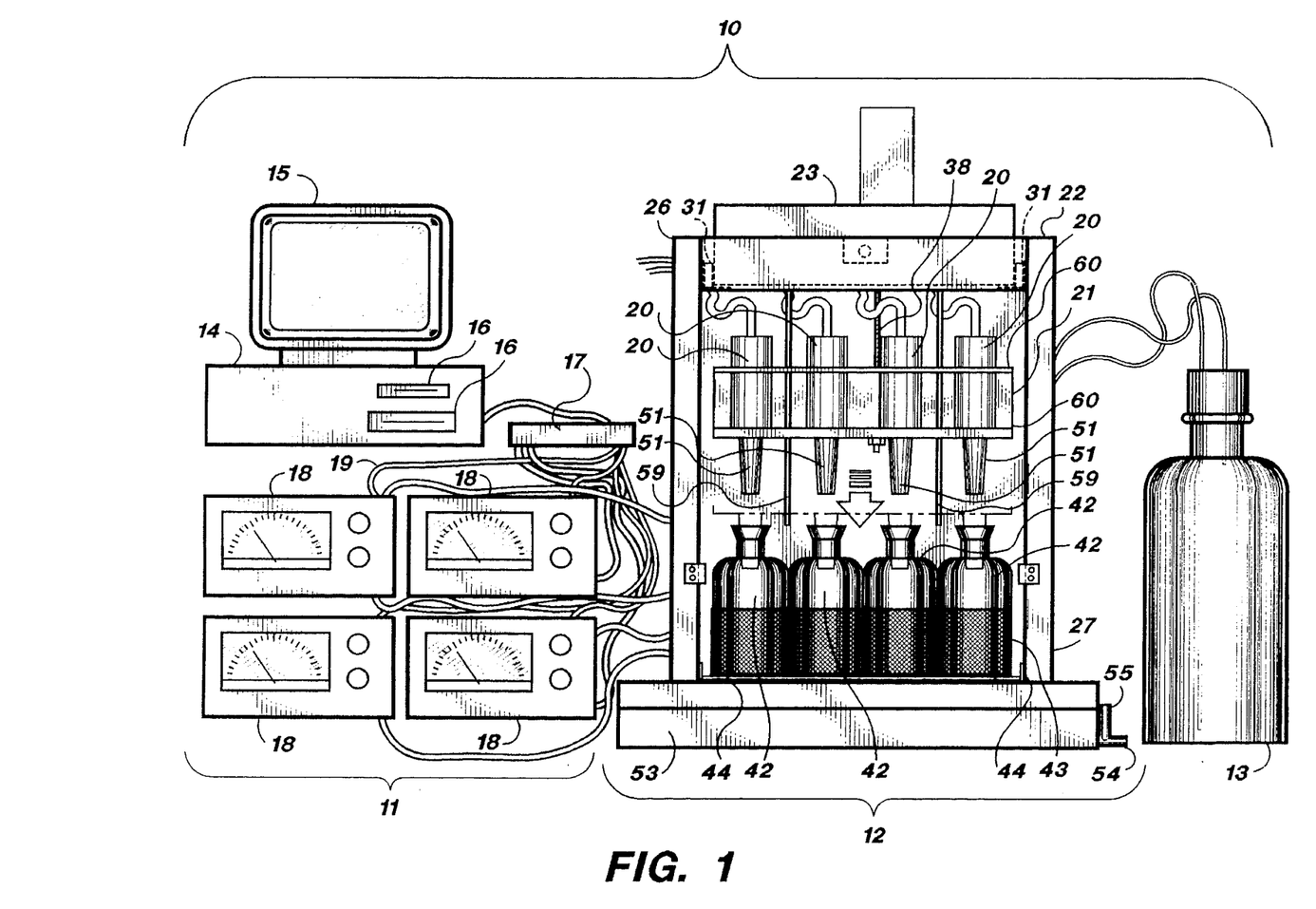
FIG. 1 is a front elevational view of the automated testing apparatus for determining the DO and BOD values of multiple test samples.
Figure 2:
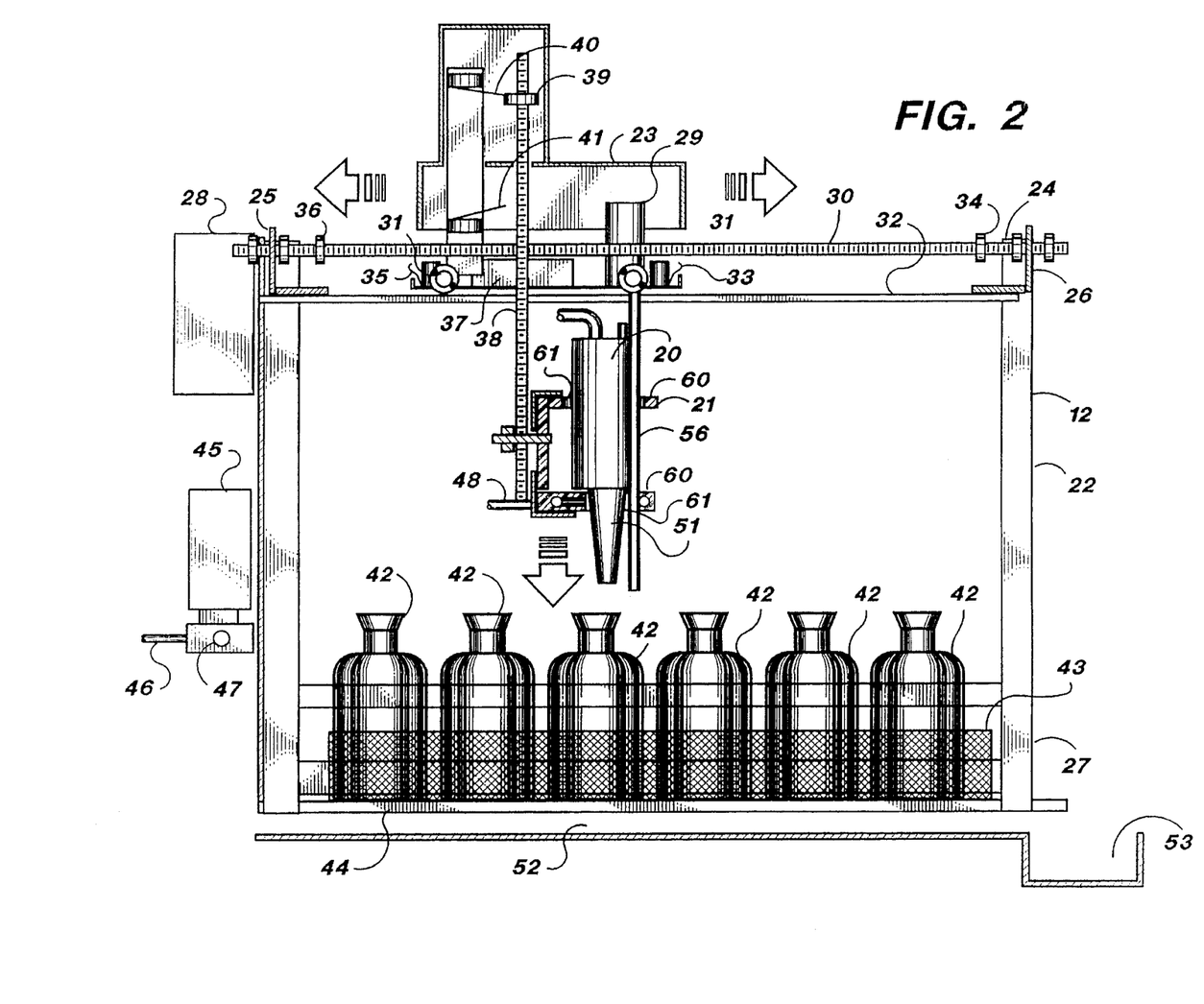
FIG. 2 is a side elevational view of the automated testing apparatus schematically showing the robotic sampling system portion of the apparatus.
Figure 3:
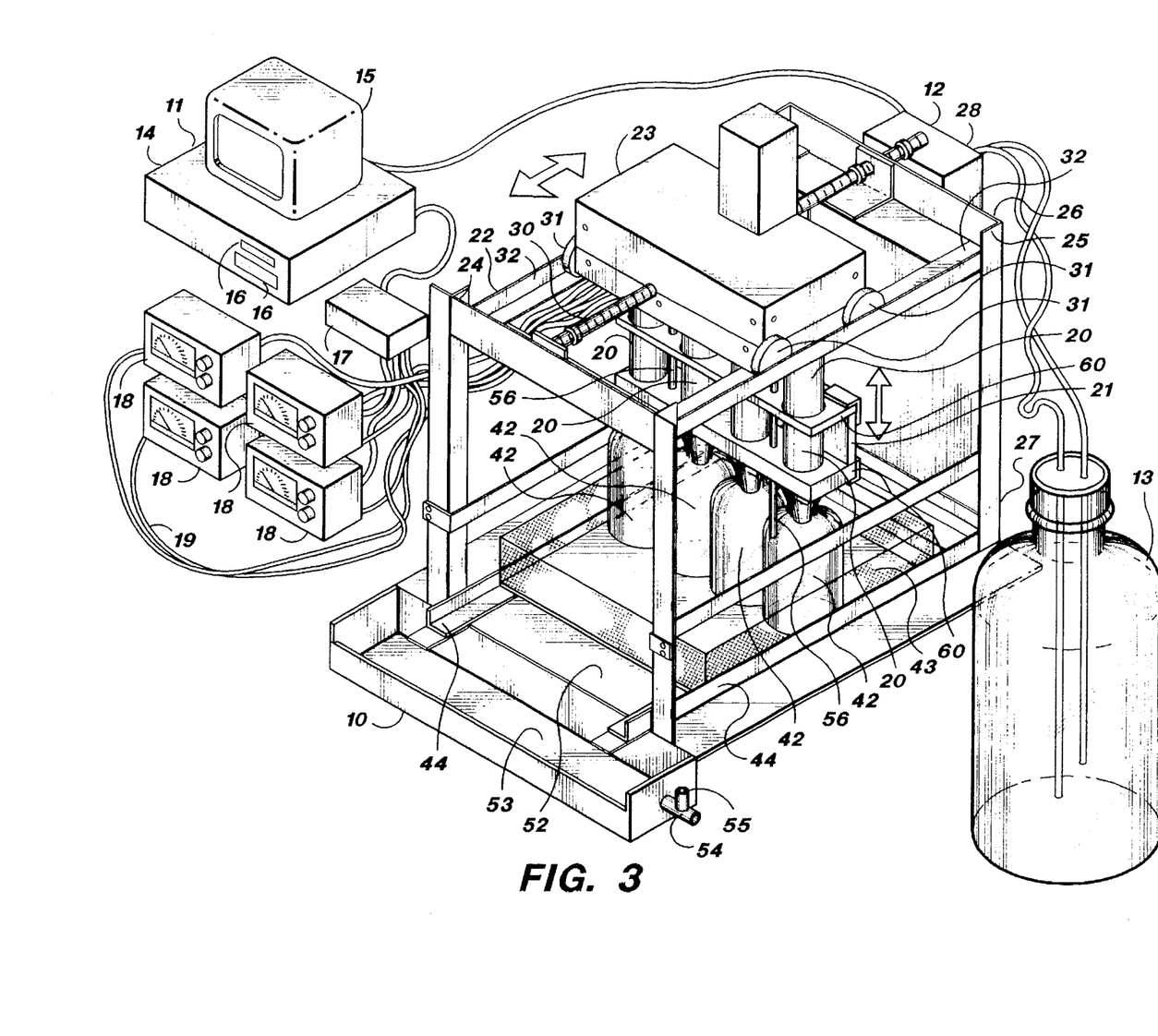
FIG. 3 is a perspective view of the automated testing apparatus for determining the DO and BOD values of multiple test samples.

The frame 22 is adapted to contain several sets of test sample containers 42, which contain the samples to be tested for DO. These test sample containers are generally standard BOD bottles, such as those described under the "5-Day BOD Test (Standard Methods for Examination of Water and Wastewater). Ideally, the bottles conform to ASTM E438, type I, Class B, Borosilicate Glass. The sets of test sample containers 42 are positioned adjacent one another within a sample tray 43, which is supported on the frame 22 by tray supports 44. The mounting plates 60 of the robotic arm 21 are configured to hold the probes 20 in positions complementary to the positions of the test sample containers 42 within the set. Thus, the robotic drive system 23 can index the probes 20 from set to set as the robotic arm 21 moves towards the front of the frame 24 or the rear of the frame 25, inserting the probes into each test sample container 42 within the set. In the preferred embodiment of the invention, the sets of test sample containers 42 are in row form (as illustrated by the single set shown in FIG. 3), and then each row is placed adjacent and parallel to another row in the sample tray 43.

For convenience, it is recommended (though not required) that a sample tray 43 be provided. The sample tray 43, which is made of mesh or a similar foraminated material, may be removed from the tray supports 44 and also removed entirely from the frame 22 so that test sample containers 42 may be removed from (and inserted into) the sample tray 43 as desired. The sample tray 43 is especially helpful when the multiple sets of samples within the tray are to be incubated. The entire sample tray 43 can then be removed and the samples can all be incubated together, minimizing the chances of misplacing samples within the set.

Figure 4:
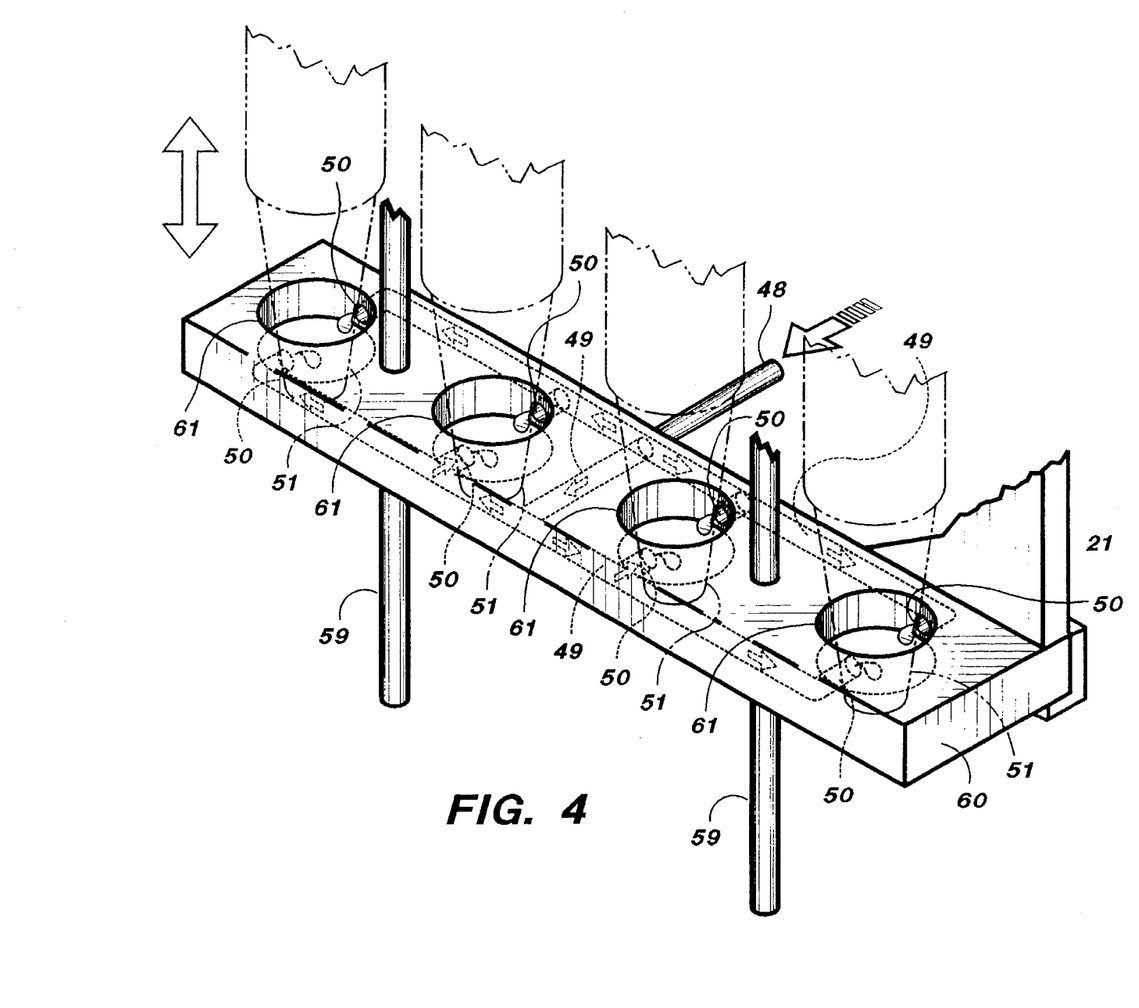
FIG. 4 is a partial perspective view of the robotic arm showing the probe rinsing mechanism.

The robotic arm 21 is also equipped with cleaning means for cleaning and rinsing the probes 20 between DO measurements so that sample residue from prior tests can be washed away, preventing its interference with later test sample analysis. These means are illustrated in FIG. 4. A wash pump 45 is situated at the rear of the frame 25. The wash pump 45 is a small gear pump which can be actuated to pump distilled water or another cleaning fluid from the rinse reservoir 13 through a pump inlet 46. When the robotic arm 21 has translated so that the probe tips 51 are oriented over, but between, two rows of test sample containers 42, the wash pump 45 may be activated so that the probe tips 51 are cleaned. The cleaning fluid is pumped through a pump outlet 47 to a pump feed line 48, where it flows through nozzle feed ducts 49 and is squirted out sprayer nozzles 50 towards and onto probe tips 51. The cleaning fluid then drips down from the probe tips 51, falling between the rows of test sample containers 42. Thus, the probe tip rinsing process is able to clean the probe tips 51 without diluting or contaminating the test samples, and no dedicated wash area is necessary. The used cleaning fluid falls onto and through the sample tray 43 and into a drain basin 52. The drain basin 52 then empties the used cleaning fluid into a drain trough 53. The drain trough 53 can be periodically emptied, or it can be automatically emptied by use of a drain line 54. A drain vent 55 may be attached to the drain line 54 to facilitate drainage through the drain line 54 despite the presence of air within the drain line 54.

Operation Of The Automated DO/BOD Analyzer

The automated DO/BOD analyzer 10 is a computer controlled robotic instrument and software system designed to automate Dissolved Oxygen (DO) and Biochemical Oxygen Demand (BOD) testing and analysis of samples. The measurement, analysis, control, and storage (MACS) system 11 includes menu-driven software which runs on the PC 14. This software serves as control means which controls the robotic sampling system 12 wherein the sample testing occurs, allowing easy monitoring and storage of sample testing and analysis results. It also serves as part of the data means for receiving, processing, and manipulating sample test data. To better understand the application of the automated DO/BOD analyzer and the many options offered by its software menus, the following summarizes a typical daily application of the automated DO/BOD analyzer 10.

DO Analysis: First, the analyst uses a worksheet menu option to prepare a daily worksheet containing a list of names (or numbers) of samples to be tested and the sample volume (dilutions) to be used. This list of sample names and dilutions can be retrieved from a previous worksheet (which is stored in the PC 14) and edited to reflect the current day's samples, or an entirely new set of names/dilutions can be generated. If the analyst so chooses, the worksheet may also include such information as the date and time, the name of the analyst, the status of the DO readings (i.e. initial or final DO), the desired filename for storing the worksheet, etc. Once the daily worksheet has been prepared, it may be stored in the PC 14, and printed to disk using the PC disk drive(s) 16 and also to paper if desired. The automated DO/BOD analyzer 10 fills in the daily worksheet with DO test results as tests are run, doing so either continuously or at intervals at different periods during the day. The stored DO measurements can later be used to calculate BOD.

After the daily worksheet is prepared, the DO meters 18 are preferably calibrated to insure accurate test results. Such calibration is effected by filling test sample containers 42 with calibration water having a known DO content (as determined by, e.g., the Winkler titration procedure, which is known to the art) and placing them in a row in the sample tray 43. The analyst then selects a calibration menu option from the software menu. The robotic sampling system 12 then lowers the robotic arm 21 so that the probe tips 51 of the probes 20 enter the test sample containers 42 and contact the calibration water therein. The DO meters 18 then obtain DO measurements, which are sequentially read by the PC 14 and displayed on the PC monitor 15. The analyst can observe the DO measurements and determine whether they are in accordance with the DO of the calibration water. If the measurements disagree, the DO meters 18 can be adjusted so that the correct measurements are displayed. After numerous tests are run, the analyst may wish to repeat this calibration procedure in order to insure that no drift has occurred in the calibration of the DO meters 18. Ideally, the calibration of the DO meters 18 is checked after each sample tray 43 of samples has been tested.

When the calibration procedure is completed, the analyst may prepare the samples specified on the daily worksheet. The analyst fills the test sample containers 42 with the samples specified by the worksheet, adds the dilution water if needed, and then places the test sample containers 42 row by row into the sample tray 43. The sample tray 43 is then placed on the tray supports 44 within the frame 22 of the robotic sampling system 12. Typically, the analyst will fill only a single row of the sample tray 43 with test sample containers 42, place the sample tray 43 within the frame 22, and choose a fill delay option from the menu which allows a fill delay time to be set. This causes the robotic sampling system 12 to stall the motion of the robotic arm 21 indefinitely (or for a set time period) after testing each row of samples. This allows the analyst to begin testing without filling the entire sample tray. The analyst may then fill only the first row of samples in the sample tray 43, start the testing operation, and then fill in subsequent rows of samples in the sample tray 43 as the robotic sampling system 12 tests the previous row and then stalls.

To begin the testing operation, the analyst selects reader options from the menu. In the preferred embodiment of the invention, the monitor 15 displays prompts to enter the analyst's name or initials, confirm the file name the worksheet test results are to be stored under, and enter the initial number of test sample containers 42 within the sample tray 43. The robotic sampling system 12 then starts the automated reading process, lowering the robotic arm 21 so that the probe tips 51 of the probes 20 each enter a respective test sample container 42 within a row of test sample containers 42 contained in the sample tray 43. If the entire sample tray 43 is not filled at this time, the analyst may begin to fill an additional row of test sample containers When the probe tips 51 enter the test sample containers 42, the MACS system 11 takes DO readings from each test sample container 42 in the row. However, the analyst can also select a read delay option which will direct the program to let the probes 20 wait for a chosen period of time within the sample before taking measurements. Typically, a 90 to 120 second delay is chosen. This allows the probe tips 51 to equilibrate with the sample before DO values are measured. The analyst can also select a read number option which determines whether each probe 20 takes one reading or several from each test sample container 42. In generals several readings are recommended, and preferably each probe 20 will take ten readings from each sample and then the PC 14 will average the results of the ten readings. In addition, the read number option can also tabulate the deviation among the several measurements for each test sample to check the performance of the probes 20. For example, the average and standard deviation of ten readings by one probe 20 can be compared at 30b second intervals to evaluate the probes response time and noise level. This is useful when evaluating if the probe 20 needs to be cleaned or replaced with a new probe 20.

After reading is completed, the robotic arm 21 is automatically lifted up by the robotic sampling system 12 to remove the probe tips 51 of the probes 20 from the row of test sample containers 20. The measured DO values are displayed on the monitor 15. The measurements are displayed along with a prompt asking whether the analyst wishes to accept the measured values and continue reading the next set of samples. This prompt remains on the monitor 15 for as long as the fill delay time is set. If an error occurred or if for some other reason the analyst is dissatisfied with the DO measurements of a row, he may choose an override menu option which returns the probes 20 to the row and allows the rereading of DO values. For example, the readings may reveal that some samples are supersaturated. The analyst may desaturate the sample(s) (or take other corrective action as necessary) and then direct the DO/BOD analyzer 10 to reread the samples. When the analyst accepts the readings (or when the fill delay time expires), the PC 14 stores the readings to disk and/or paper. The reading(s) for each sample may be stored in the worksheet along with the name/number of the sample. If selected at the start of the process, the PC 14 may also save other information such as the sample volume/contents, date, time, name of the analyst, whether the reading is an initial or final DO, the desired filename, etc.

The DO/BOD analyzer 10 will then proceed with a rinse cycle. The probes 20 are then advanced halfway toward the next row of test sample containers 42 and partially lowered. The wash pump 45 is actuated to rinse the probe tips 51 for some period of time, which may be set by the analyst at program startup (generally 1–12 seconds). The probes 20 are then elevated and advanced to the next row of test sample containers 42 to begin reading from this new row.

The testing process is continued until all samples in the sample tray 43 have been tested or the analyst-specified number of rows have been tested. The analyst can stop the process at any time and reread a set of test sample containers 42 using the override option. When an entire tray has completed testing, the program may supply a prompt to insert a new sample tray 43 full of new test sample containers 42. It may also request whether the analyst wishes to recheck the calibration of the DO meters 18. When testing is completed, the analyst can then retrieve the completed daily worksheet onto the PC monitor 15 and edit it for any changes in sample order or dilution volumes that may have been made during the process. Additional sample sets can be added to the worksheet throughout the day.

BOD Analysis: The software menu allows the analyst to select options which utilize the aforementioned DO measurement process to read and store initial DO measurements and also final DO measurements. The DO/BOD analyzer 10 may then use the initial and final DO values to calculate the biochemical oxygen demand (BOD) of the samples.

First, after making initial DO readings using the aforementioned process, the samples must be incubated for some time period until the final DO reading is to be taken. After a sample tray 43 full of samples has been analyzed for initial DO, the analyst caps the test sample containers 42, adds water seals, and places the sample tray 43 into an incubator.

Second, after the desired amount of incubation time has passed and the final DO measurements are to be made, the analyst prepares the DO/BOD analyzer 10 to make final DO measurements. Upon selecting the final DO option, the program prompts to ask whether the final DO values are to be measured for the samples whose initial DO values were measured a set number of days ago (i.e., 5 days ago). The analyst may confirm or edit the initial DO date. The program then accesses the daily worksheet with the specified initial DO date containing the initial DO measurements for that date.

Third, the analyst prepares the samples for final DO testing. The analyst retrieves the incubated samples, removes the water seals and caps from the test sample containers 42, and replaces the sample tray 43 into the robotic sampling system 12.

Fourth, the DO/BOD analyzer 10 may provide prompts to insure that the final DO test will be correctly run. In the preferred embodiment of the invention, the analyst must enter the number of rows of sample containers to be tested and the bottle numbers of the first row of test sample containers 42. The program then checks to verify that the analyst is testing the correct tray and that the test sample containers 42 are being tested in the proper order (e.g., so that the tray is not placed in the robotic sampling system 12 with the bottles in an order backwards from the order in which they were tested).

The DO/BOD analyzer then repeats the DO measurement process to obtain the final DO readings and calculate the BOD values for the samples. The program includes an algorithm that can calculate the BODs for a set of samples by determining the oxygen depletion, correcting the seed depletion (for seeded samples), multiplying the oxygen depletion by the dilution factor, and averaging all sample dilutions that meet the appropriate depletion criteria, thereby producing a single reportable value for a given sample name. This BOD calculation process is outlined in Standard Methods for the Examination of Water and Wastewater, 18th ed. 1992, edited by Arnold E. Greenberg et al. The program calculates and applies any applicable seed factors. Throughout the final DO measurement and recordation process, the program stores both the final DO values and the BOD value (calculated from the initial and final DO values) on the worksheet. Any BOD values that do not meet acceptable oxygen depletion criteria are detected by the program and highlighted by an asterisk (or another such "flag") following the recorded value in the worksheet. The analyst can store, print, transfer, etc. the worksheet and the calculated BOD measurements as desired.

It is understood that the invention is not confined to the particular construction and arrangement of parts herein illustrated and described, but embraces such modified forms thereof as come within the scope of the following claims.

What is claimed is:

1. An automated testing apparatus for determining the dissolved oxygen (DO) values of test samples comprising:

a. a frame structure;

b. a sample set which contains a row of multiple spaced test sample containers and which rests adjacent to the frame structure;

c. a moveable robotic arm which is supported by the frame structure and which is adapted to move towards and away from the sample set;

d. a DO probe;

e. attachment means on the robotic arm for releasibly attaching the DO probe to the robotic arm in such a position that the DO probe, once releasibly attached, may communicate with a test sample container within the sample set when the robotic arm moves towards the sample set;

f. at least one sprayer nozzle on the robotic arm for administering a fluid rinse to a DO probe releasibly attached to the robotic arm; and     g. control means for controlling the robotic arm and delivering fluid rinse through the sprayer nozzle when the robotic arm rests in a plane between adjacent test sample containers, thereby allowing the fluid rinse to clean the DO probe and drain from the DO probe between the adjacent test sample containers.

2. The apparatus of claim 1 further comprising a DO probe releasibly attached to the robotic arm by use of the attachment means.

3. The apparatus of claim 2 further comprising data means for receiving and manipulating data from the DO probe.

4. The apparatus of claim 3 wherein the data means and the control means is the same.

5. The apparatus of claim 3 wherein the data means comprises a DO meter interfaced with the DO probe and a programmable computer interfaced with the DO meter.

6. The apparatus of claim 3 wherein the data means comprises a programmable computer.

7. The apparatus of claim 2 comprising a plurality of DO probes.

8. The apparatus of claim 1 further comprising a drain basin for removing fluid rinse from the apparatus.

9. The apparatus of claim 8 wherein the drain basin is located beneath the test sample containers.

10. The apparatus of claim 1 further comprising a sample tray adapted to contain the sample set therein.

11. The apparatus of claim 10 wherein the sample tray is foraminated.

12. The apparatus of claim 1 wherein the sprayer nozzle comprises a duct within the*interior of the mounting plate.

13. The apparatus of claim 12 wherein the sprayer nozzle exits upon the probe aperture.

14. The apparatus of claim 1 wherein the sample set comprises a row of test sample containers.

15. The apparatus of claim 1 further comprising a plurality of sample sets, with each sample set positioned adjacent to at least one other sample set so that the several sample sets rest along a substantially linear path, and wherein the robotic arm is also adapted to move in a direction generally parallel to the linear path.

16. The apparatus of claim 1 further comprising a rinse reservoir for holding fluid rinse, and a pump in fluid communication with the rinse reservoir and the sprayer nozzle.

17. An automated testing apparatus for determining the dissolved oxygen (DO) values of multiple test samples comprising:

a. a tray adapted to contain rows of multiple spaced test sample containers, wherein the rows are oriented in a parallel array along a linear path;

b. a moveable robotic arm located above the tray which may translate downward towards the tray and upward away from the tray and also in a dimension generally parallel to the linear path;

c. DO probes;

d. attachment means for releasably attaching the DO probes onto the robotic arm;

e. rinsing means for rinsing the DO probes which are releasibly attached to the robotic arm, the rinsing means being operative when the robotic arm positions the DO probes in a plane between adjacent test sample containers; and f. a drain basin situated beneath the tray.

18. The apparatus of claim 17 wherein the tray is foraminated.

19. An automated testing apparatus for determining the dissolved oxygen (DO) values of test samples resting within respective test sample containers, the apparatus comprising:

a. a moveable robotic arm adapted to index between respective test sample containers;

b. at least one mounting plate attached to the robotic arm, the mounting plate having a probe aperture therein for receiving a DO probe;

c. at least one sprayer nozzle on the mounting plate, the sprayer nozzle being in communication with a rinse fluid source and being directed toward the probe aperture;

d. control means for indexing the robotic arm and activating the sprayer nozzle to deliver rinse fluid when the robotic arm is located in a plane between respective test sample containers; and e. a drain basin located beneath the test sample containers, the drain basin being adapted to catch rinse fluid delivered from the sprayer nozzles.

20. The apparatus of claim 19 wherein the sprayer nozzle is integrally formed within the mounting plate.

21. The apparatus of claim 19 further comprising a foraminated tray adapted to support the test sample containers above the drain basin.

22. The apparatus of claim 19 wherein the control means comprise a personal computer.

* * * * *